United States Patent [19]

Eichmiller

[11] Patent Number: 5,525,647
[45] Date of Patent: Jun. 11, 1996

[54] METHOD AND DEVICE FOR CONTROLLABLY AFFECTING THE REACTION OF DENTAL ADHESIVES

[75] Inventor: Frederick C. Eichmiller, Ijamsville, Md.

[73] Assignee: American Dental Association Health Foundation, Chicago, Ill.

[21] Appl. No.: 283,833

[22] Filed: Aug. 1, 1994

[51] Int. Cl.⁶ .................................................... A61C 3/00
[52] U.S. Cl. ............................ 523/105; 15/167.1; 433/89
[58] Field of Search .............................. 523/105; 433/89; 15/167.1

[56] References Cited

U.S. PATENT DOCUMENTS

| | | | |
|---|---|---|---|
| 4,514,527 | 4/1985 | Bowen | 523/116 |
| 4,521,550 | 6/1985 | Bowen | 523/116 |
| 4,588,756 | 5/1986 | Bowen | 523/116 |
| 4,659,751 | 4/1987 | Bowen | 523/116 |
| 4,995,540 | 2/1991 | Colin et al. | 433/90 |
| 5,270,351 | 12/1993 | Bowen | 523/116 |
| 5,320,886 | 6/1994 | Bowen | 428/34.1 |

FOREIGN PATENT DOCUMENTS

| | | | |
|---|---|---|---|
| 3808853 | 10/1989 | Germany | 15/167.1 |
| 0000506 | 1/1976 | Japan | 15/167.1 |
| 0563767 | 7/1975 | Switzerland | 433/90 |

OTHER PUBLICATIONS

Bowen, et al., "Development of an Adhesive Bonding System," Operative Dentistry, Supplement 5:75–80 (1992).
Getz, Compodent™ Composite Dental Restorative Material, Promotional Material (1974).
Miniotis et al., "Molar Efficiency of Chlorinated NPG Substitutes in Dentin Bonding", Journal of Dental Research, vol. 72, pp. 1045–1049, Jun. 1993.

*Primary Examiner*—Paul R. Michl
*Assistant Examiner*—Andrew E. C. Merriam
*Attorney, Agent, or Firm*—Banner & Allegretti, Ltd.

[57] ABSTRACT

This invention relates to dental restorative materials and adhesives, and particularly relates to the control of chemical reactions in chemically initiated dental restorative materials. The invention includes a method for controllably affecting the reaction of a chemiclly initiated liquid dental adhesive, resin or restorative material comprising mixing the adhesive, resin or retorative material with an instrument, or in a mixing container, at least a portion of which instrument or container has been impregnated with a reaction affecting compound of predetermined amount to accomplish the intended reaction effect. Devices and kits for use in the inventive methods are also disclosed. The present invention affords both efficiency and greater control in applying dental adhesives, resins or restorative materials, reduces the time necessary for mixing and dispensing solutions and allows the components of the dental adhesive, resin or retorative material to be stored in a more stable form.

12 Claims, No Drawings

METHOD AND DEVICE FOR CONTROLLABLY AFFECTING THE REACTION OF DENTAL ADHESIVES

This invention was supported in part by National Institute of Health grants NIDR R37 DE05129 and NIDR P50 DE09322 to the American Dental Association Health Foundation. The government may have certain rights to this invention.

BACKGROUND OF THE INVENTION

1. Field of the Invention

This invention relates to the field of dental restorative materials and adhesives. More particularly, it relates to the control of chemical reactions in chemically initiated dental restorative materials.

2. Description of the Prior Art

Dental polymeric restorative materials and adhesives are cured by the addition of very small amounts (e.g., 0.01 to 5.0 weight percent) of catalysts and co-initiators. See Bowen U.S. Pat. Nos. 5,270,351; 4,659,751; 4,588,756; 4,521,550; 4,514,527 and allowed U.S. patent application Ser. No. 07/791,999, filed Nov. 14, 1991. Most initiating systems consist of two active components; a free-radical initiator such as benzoyl peroxide or camphorquinone and a free radical-generating co-initiator consisting of a secondary or preferably tertiary aromatic amine or an aliphatic amine. Combining the peroxide and amine or quinone and amine, plus exposure to light, results in the generation of radicals that causes the polymerization of the adhesive, restorative material, and/or other monomer(s). The peroxide and amine components are generally separated during storage to prevent premature polymerization. This separation is done by mixing the small fractions of each of the coinitiators with separately stored portions of the resin or other ingredients. These two separate portions are then combined immediately before use to initiate the free radical-polymerization reaction under controlled conditions.

In some resin systems, the storage stability of the initiators is limited by exposure to oxygen or elevated temperatures. Solutions of certain amine compounds used in dental adhesives, such as NPG (N-phenylglycine), are known to degrade within a few days when exposed to air. Salt solutions of these compounds, such as the magnesium or sodium salt in acetone, are relatively stable for a number of months when exposed to air. The solid salt forms, however, are the most stable of all and can be stored exposed to air for years without adversely affecting them.

Several approaches have been used to store and deliver oxygen-sensitive adhesive materials. Products using NPG have been packaged in sealed glass syringe capules under argon to prevent oxygen contamination and exposure. Products using NPG-GMA (N-phenylglycine glycidylmethacrylate) have been packaged under inert gas in sealed glass ampules to prevent oxygen exposure. Both methods are expensive from the standpoint of manufacture and inconvenient for the operator to dispense and use. Other products deliver the amine as an acetone solution of the sodium or magnesium salt of NTG-GMA (N-tolylglycine glycidylmethacrylate). The solutions have a shelf life of several months at room temperature that can be extended to over one year if refrigerated. These solutions, however, must still be dispensed and mixed with a corresponding acidic monomer, or monomer containing a coinitiator, to initiate polymerization.

Better approaches to the difficulties associated with the procedures discussed above have not been forthcoming. In the mid-1970's, Teledyne Dental Products Company of Chicago produced a dental restorative kit, sold under the trademark "COMPODENT", that had a paper mixing pad saturated with amine initiator. The product had a brief market life of about a year because problems developed in achieving proper proportioning of the initiators and adequate mixing using the system with viscous composites.

SUMMARY OF THE INVENTION

Dental restorative materials, adhesives and related products are used in very small quantities and contain even smaller amounts of additives, such as catalysts, stabilizers, antioxidants, and co-initiators. Some of the major problems with existing products of this type are the number of steps required to mix and apply them and the short shelf life of the components. It is a particular problem in delivering resin systems that use oxygen-sensitive materials in solution to deliver products with a long shelf life that can be conveniently manufactured, dispensed, mixed and applied.

The present invention simplifies the packaging and application of liquid dental restorative materials, adhesives and related compositions. It improves the storage stability of such materials by allowing sensitive components to be stored in the more stable solid form and still be delivered in a convenient manner. The invention includes a method for controllably affecting the reaction of a chemically initiated liquid dental adhesive, resin or restorative material comprising mixing the adhesive, resin or restorative material with an instrument, or in a mixing container, at least a portion of which instrument or container has been impregnated with a reaction affecting compound of predetermined amount to accomplish the intended reaction effect. As used herein, the term "reaction affecting compound" means any compound that initiates, accelerates or catalyzes a desired chemical setting reaction of a liquid dental restorative material, adhesive or related compound. In a preferred embodiment, the impregnated portion of the instrument or container is of conformation and size such that substantially all of the reaction affecting compound is contacted with the adhesive, resin or restorative material during mixing.

Preferably, the chemically initiated liquid dental adhesive, resin or restorative material is a monomer which is free radically initiated to polymerize. The reaction affecting compound may be, e.g., a catalyst, such as a free radical initiator, a stabilizer, an antioxidant, and/or a co-initiator. The instrument or mixing container is preferably a bristle brush, sponge, absorptive pledget, mixing container or other absorptive application instrument which may be used to mix and/or transfer and apply the dental adhesives or film-forming resins or other restorative materials to the tooth or other treatment surfaces. Before use, the instrument or mixing container has been impregnated with one or more reaction affecting compounds, e.g., catalyst or polymerization initiator components, in the correct quantity to adequately affect the reaction of a single dispensed aliquot of adhesive, resin or restorative material. In this context, the term "impregnated" is intended to encompass any means of depositing the reaction affecting compound on the instrument or mixing container, such as impregnation, soaking followed by evaporation, coating or precipitation.

For example, the method of the invention may be practiced by dispensing the adhesive and/or other monomer into a dish or well and stirring for a few seconds with an initiator impregnated brush or sponge. The stirring motion will dissolve and mix the initiators with the monomer and begin polymerization. Achieving economy of instrumentation, this same applicator is then used to transfer the catalyzed monomer(s) to the prepared tooth or other site where it is applied to the surface(s) by brushing or painting on one or more layers. The monomer then completes polymerization in the normal working and setting time designed for that material.

The invention also contemplates a device for controllably affecting the reaction of a chemically initiated liquid dental adhesive, resin or restorative material comprising an instrument or mixing container which has been impregnated with a reaction affecting compound of predetermined amount to accomplish the intended reaction effect for a single application aliquot of adhesive, resin or restorative material. The instrument or mixing container which is impregnated with a reaction affecting compound is preferably of size and conformation such that routine mixing of the liquid dental material with the instrument or in the container results in contact between the dental material and substantially all of the reaction affecting compound which is impregnated onto the instrument or container.

The invention also includes a kit for performing dental restorative procedures comprising: (a) a chemically initiated liquid dental adhesive, resin or restorative material; and (b) an instrument or mixing container impregnated with a reaction affecting compound of predetermined amount to accomplish an intended reaction effect for a single dispensed aliquot of adhesive, resin or restorative material.

The present invention overcomes the storage limitations and dispensing inconvenience of the prior art systems. For example, it delivers the solid form of an oxygen-sensitive co-initiator, such as the magnesium salt of NTG-GMA, in a clinically convenient manner. All of the prior art dental adhesive systems require a brush or sponge to apply the liquid materials to the treated surfaces, and most systems use the same applicator to mix the components prior to placement. In accordance with the method described in the present invention, the co-initiator is precipitated directly onto the mixing and applying instrument, such as a sponge or brush tip. A single-component formulation of the liquid adhesive or film forming material can be agitated with the impregnated application instrument and applied to the surface with that same instrument. The invention thus improves storage stability by using the more stable solid forms of these initiators and simplifies the delivery by eliminating the need to mix separate solutions prior to placement. As compared with the paper mixing pads formerly sold under the trademark "COMPODENT" by the Teledyne Dental Products Co. of Chicago, the present invention solves the proportioning problem by using application instruments saturated with controlled amounts of initiator or the like that is completely consumed on mixing. Use of the invention including liquid or solvent containing materials also leads to rapid and thorough mixing.

In general, the present invention affords both efficiency and greater control as compared with the prior art. It is an advantage of the invention that one less solution must be dispensed and applied at the time of a restorative procedure.

It is also an advantage of the invention that less time is required for mixing and dispensing solutions.

It is a further advantage of the invention that standardized amounts of the reaction affecting compounds, such as amines, can be coated onto the instrument or mixing container, such as a brush, sponge, pledget or other application device and delivered during the application procedure.

It is a still further advantage of the instant invention that control of the adhesive/solvent ratio can be obtained.

It is an additional advantage of the invention that the components can be stored in a more stable solid form.

It is a further advantage of the present invention that for dentin bonding systems, composite dentin-strengths obtained with the inventive method are comparable to those from the conventional protocol of mixing two solutions.

DESCRIPTION OF THE PREFERRED EMBODIMENTS

The invention is applicable to dental procedures involving the use of chemically initiated adhesives, resins (including film-forming resins), restorative materials and similar dental materials. The invention is intended for use with liquid systems of restorative materials, adhesives, and resins. Although the invention is specifically useful with chemically initiated systems, chemical initiation may be only an aspect of the initiation protocol, and light initiation may also be involved. Most commonly, the dental materials employed in the procedure will be polymerizable monomers, frequently free-radical polymerizable monomers. In such systems, the most widely used additives are catalysts, stabilizers, antioxidants and co-initiators. Exemplary catalysts are benzoyl peroxide and camphorquinone. The co-initiators are often free-radical co-initiators, typically secondary amines, aliphatic amines or most preferably, tertiary amines. N-phenylglycine (NPG) is an example of an amine compound used in some dental adhesives.

The instrument or mixing container which is impregnated with the reaction affecting compound such as a catalyst, stabilizer, antioxidant or co-initiator may take many forms. Generally, any device which can be controllably impregnated with a predetermined amount of reaction affecting compound calculated to accomplish the intended reaction effect for one aliquot of the dental material and which can conveniently serve to mix and optionally apply the dental material may be employed. One example of an instrument for mixing and applying the dental material is a bristle brush with either hollow or solid lumens. Most preferably, the brush would have hollow lumens. Another example of an application instrument is a sponge, optionally on the end of a wand. Other instruments and mixing containers include absorptive pledgets, mixing wells and mixing containers, as well as other absorptive application instruments to transfer and apply the treated dental material. The instrument or mixing container is impregnated, coated, precipitated, saturated or otherwise imbued with a controlled amount of reaction affecting compound of predetermined amount correlated to an aliquot of the liquid dental material with which it is mixed, so as to result in relatively reproducible levels of the reaction affecting compound in the post-mixing dental material. The size and conformation of the impregnated portion of the mixing instrument or mixing container are designed to facilitate this relatively reproducible complete mixing.

An example of manufacture of an embodiment of this invention would be the fabrication of an application brush impregnated with the co-initiator NTG-GMA. The more stable magnesium salt of this material is first dissolved to form a concentrated solution in acetone. The concentration of the solution can be adjusted to provide the correct quantity precipitated on and in the brush bristles. Disposable brush tips made from nylon brush bristles with one or more hollow lumens, such as model ME 1390HA trilocular filaments produced by DuPont Polymers of Wilmington, Del., and sold under the trademark "TYNEX", are then immersed into this solution and the lumens filled with the solution by capillary action. The bristle lumens can also be filled prior to being fabricated into disposable brush tips. Once saturated, the brush tips are removed from the solution and the acetone solvent is evaporated in air, an inert gas atmosphere, by vacuum desiccation, or in a low temperature oven. The solid magnesium salt will then precipitate on the surfaces of the bristle fibers and within the hollow lumens. Using bristles with hollow lumens will protect the solid material from being dislodged.

The impregnated brush tips are then color coded or labeled for use with a monomer formulation, such as PMDM (the addition reaction product of pyromellitic dianhydride with 2-hydroxyethylmethacrylate) or PMGDM (the addition reaction product of pyromellitic dianhydride with glyceroldimethacrylate), that is compatible with the NTG-GMA amine salt.

A similar method can be used to impregnate sponge or pledget applicators, or the surface of the mixing well or container. The amount of material delivered with each disposable instrument or container can be controlled by the size, length, or volume of the instrument or container and by the concentration of the solution used to impregnate it. The precipitated material can be further protected from loss or displacement by coating it with a film or binder soluble in the monomer adhesive mixture. Alternatively, the applicator tips and the like could be protected with optionally opaque disposable plastic covers.

EXAMPLE 1

For examples of this new application procedure, two types of brush tips were evaluated: regular, solid bristle (Anchor Brush, Inc.) and a trilocular cross-section nylon filament (sold under the trademark Natural 410 "TYNEX" ME 1390HA, by DuPont Polymers, Wilmington, Del.). The catalyst amine chosen for this study was the magnesium salt of NTG-GMA ($Mg(NTGGMA)_2$) (Bowen et al., Development of an Adhesive Bonding System, Operative Dentistry, Supplement 5:75–80 (1992)). This catalyst is available from Myron International, Kansas City, Kans., in kits sold under the trademark "MIRAGE ABC", from Lee Pharmaceuticals, So. El Monte, Calif., in kits sold under the trademark "RESTOBOND 4", and from Pulpdent Inc., Watertown, Mass., in kits sold under the trademark "DENTASTIC". A saturated solution of $Mg(NTGGMA)_2$ in acetone was prepared.

Dentin sample preparation

Dentin samples were made by following the procedure outlined by Bowen (Bowen, R. L. Adhesive bonding of various material to hard tooth tissues. I. Method of determining bond strength, Journal of Dental Research 44:690 July–August. (1965)). Extracted, noncarious human molars that had been stored in 2% sodium azide at 5° C. were cut with a slowly rotating diamond blade (Isomet, Buehler Ltd., Lake Bluff, Ill.) under running water until a smooth dentin surface was exposed. Each test assembly consisted of a precision-fitted outer sleeve, a dentin sample mounted in acrylic resin and a plunger to which dental composite resin was applied (Miniotis et al., Molar Efficiency Study: Chlorinate NPG Substitutes in Dentin Bonding, Journal of Dental Research, 72(6):1045–1049 (1993)). A metal disc with a 19.55 $mm^2$ circular opening determined the bonding area. The dentin surfaces were finished with 320-grip abrasive such that the dentinal tubules were predominantly perpendicular to the test surfaces.

Bonding protocol

One drop of 2.5% w/w nitric acid was applied to the dentin surface and was agitated with an acid-saturated cotton pledger for 60 s. Excess solution was blown from the surface for 3–4 s with compressed air. A brush tip precoated with $Mg(NTGGMA)_2$ was dipped into a well that contained two drops of 20% w/w PMGDM (with 2.0% benzoyl peroxide (BPO), 0.2% camphorquinone (CQ), and 0.06% BHT with respect to the weight of PMGDM) in acetone. Five sequential coats of this solution were brushed onto the dentin surface with approximately 5 s between coats. The surface was allowed to sit undisturbed for 60 s and then was lightly air dried. One drop of unfilled resin (obtained from a kit sold under the trademark "MIRAGE BOND" by Myron International, Kansas City, Kans.) was applied to the dentin surface, blown thin, and light cured for 20 s.

A two-paste resin composite (Schein, Port Washington, N.Y.) was mixed in accordance with the manufacturer's recommendations and applied to the plunger. After each apparatus was assembled, a 1-kg mass was placed on the plunger for 2 min. The assembly was allowed to stand undisturbed for 20 min. and was then immersed in distilled water at room temperature overnight. The assemblies were broken with tensile loads applied at a cross-head speed of 0.5 cm/min (Instron Universal Testing Instrument, Model 1130, Instron Corp., Canton, Mass.).

The teeth were visually examined for pulp exposure after each bonding session. If the pulp horns were exposed, the teeth were replaced before the next bonding cycle.

EXAMPLE 2

Amine Amount and Solid vs. Hollow-Fiber Brush Tip Comparisons

To prepare the solid bristle brushes, solid bristle brush tips were obtained from Anchor Brush, Inc., and the solution was added drop-wise to the brush tips allowing the acetone to evaporate until the following average weights of precipitated $Mg(NTGGMA)_2$ were reached: 0.0001 g/brush, 0.0005 g/brush, 0.0007 g/brush, 0.0010 g/brush and 0.0020 g/brush. In order to increase the acetone evaporation rate, cool air was blown across the brush tips after adding each drop. The brushes were stored at room temperature overnight before use.

The trilocular hollow fiber brush tips were prepared by collecting and securing into a plastic tip with utility wax a bundle of 27 trilocular filaments sold by DuPont Polymers, Wilmington, Del., under the trademark "TYNEX". The waxed end was inserted into a plastic tip holder, and hot sticky wax was applied at the junction to secure the fibers into the holder. The fibers were initially clipped to 1.5 cm with wire cutters. A sharp razor blade was then used to neatly trim the fibers to 1 cm. This was done to ensure that the trilocular holes were completely open for the adequate uptake of the catalyst solution. The brushes were dipped into the saturated solution of $Mg(NTGGMA)_2$ in acetone for several seconds, then stored overnight in a desiccator under vacuum, to ensure complete evaporation of the acetone. Each brush tip held approximately 0.0020 g of $Mg(NTGGMA)_2$.

EXAMPLE 3

Comparisons of tensile bond strengths (TBS) obtained with the use of the solid brushes precoated with the five different amounts of amine showed that the solid brushes preloaded with the 0.0001 g of Mg(NTGGMA)$_2$ yielded significantly lower bond strengths than the other four concentrations (see Table 1 ). Mean bond strengths for amine weights between 0.0005 g and 0.0020 g were statistically indistinguishable. The overall p-value from the ANOVA (analysis of variance) was 0.0046.

TABLE 1

| Results of Duncan's Multiple Comparison Procedure | | |
|---|---|---|
| Amine weight (n) | Mean TBS MPa | [s.d. TBS] |
| 0.0007 (10) | 14.0 | 4.5 |
| 0.0020 (19) | 12.1 | 3.8 |
| 0.0005 (28) | 11.9 | 4.2 |
| 0.0010 (27) | 11.7 | 5.0 |
| 0.0001 (10) | 6.8 | 3.3 |

EXAMPLE 4

The initial test of the trilocular brushes yielded a mean TBS of 16.7 MPa (s.d.=4.8, n=8). All of these values are equivalent to or greater than those achieved using mixed solutions of these compounds.

The solid and the trilocular brush tips were then retested side by side in a randomized block design over 2 days (n=40, total). Both types of brush tips were saturated with 0.0020 g (s.d.=0.000325 g, trilocular tips; s.d.=0.000016 g, solid tips) of Mg(NTGGMA)$_2$. A basic Student t test was used to determine bond strength differences that resulted from the use of the two types of brush tips. The trilocular and solid brush tips had a mean TBS of 14.1 MPa (s.d.=5.6, n=19) and 13.6 MPa (s.d.=4.0, n=17), respectively. At the 95% level of confidence, the difference between the two means was not significant (t test, p=0.80).

EXAMPLE 5

Storage Stability Testing

An additional eight solid-bristle brush tips were prepared such that each contained approximately 0.0020 g (0.00196±0.00022 g) of Mg(NTGGMA)$_2$. These precoated tips were stored for 32 days at 45° C. before using in an accelerated aging stability test. The average tensile bond strength achieved with the stored tips was 14.9 MPa [s.d.= 2.0], which was equivalent to the previous group of freshly prepared tips.

EXAMPLE 6

Simulated Storage/Shipment Tests

A group of trilocular brush tips was tested under simulated "shipment" conditions. To simulate "shipment" conditions, the trilocular brush tips were precoated with Mg(NTGGMA)$_2$ and placed in a vial. The vial was moderately agitated for 3 minutes by hand. The average amount of Mg(NTGGMA)$_2$ lost due to the simulated "shipment" was calculated. These trilocular brush tips were then used in the bonding protocol. Before "shipment" the average amount of amine on a brush tip was 0.0011 g (s.d.=0.00085 g). After "shipment", the average amount was 0.0008 g (s.d.=0.00061 g); the average percent of Mg(NTGGMA)$_2$ remaining on a brush after "shipment" was 85% (s.d.=27%). Tensile bond strengths obtained from the use of these tips averaged 10.5 MPa (s.d.=3.2, n=10).

No simulated "shipment" condition was deemed necessary for the solid brush tips precoated with amine because the loss of amine was visibly evident whenever the solid brushes were disturbed.

EXAMPLE 7

Sponge Applicator

A dental applicating sponge was cut into cubes approximately 2.5 mm on a side to be used as impregnated carrier, mixing and applicating instruments. These sponges are commonly used in many dental products to apply adhesive resin formulations and are readily available.

Each sponge applicator was saturated by dipping in acetone and rapidly weighed to determine the weight of solvent that it could absorb and hold. The absorbed weight was approximately 20 to 25 mg of acetone. From the weight of absorbed solvent, the concentration of initiator was calculated at 8.2% in acetone to deliver enough initiator to properly catalyze a one dose increment (two drops) of an adhesive monomer. An acetone solution of initiator, the magnesium salt of NTG-GMA, of 8.2% was then made and the sponge applicators submersed in this solution. The sponges were then dried in air and by vacuum to remove the acetone solvent. The amine precipitated as a solid on the surface of the sponge void cells, and the average weight of amine contained in the sponges was 2.35±0.442 mg.

A predetermined dose volume of two drops of the adhesive monomer (PMGDM) was then dispensed into a mixing container and agitated with the previously described sponge held in a cotton plier. This caused the Mg(NTGGMA)$_2$ amine to mix with the adhesive monomer containing the appropriate co-initiators, camphorquinone and benzoyl peroxide, thereby starting the polymerization reaction. The mixed and activated solution of adhesive was then directly painted onto the tooth surface in one or more coats with this same applicator sponge. The sponge was then discarded after use. Nine shear bond strengths of composite to dentin were determined using this method of application.

A group of nine control specimens were made for comparison by mixing the adhesive monomer directly with a 5% acetone solution of the Mg salt of NTG-GMA.

The results of shear bond testing showed the sponge group had an average strength of 12.79±3.34 MPa while the control group had an average strength of 14.21±5.37 MPa. There was no statistically significant difference between the two sets of results. The pre-impregnated sponges yielded bond strengths equivalent to the control dual mixed solutions method, while offering greater storage stability, streamlined packaging and simpler mixing protocols.

EXAMPLE 8

Pre-impregnated Mixing Container

Pre-impregnated mixing containers were prepared using small plastic mixing wells. Plastic mixing wells arc commonly supplied with dental adhesive and liquid resin materials for mixing and dispensing of the liquid components. These wells are preformed depressions in a plastic sheet leaving a well of sufficient volume to conveniently contain and allow mixing of a single dose-increment of adhesive or liquid resin material. The invention was practiced by supplying these disposable mixing wells with a pre-dispensed amount of initiating compound precipitated on the inside surface of the well.

A calculated single dose amount of amine co-initiator, Mg(NTGGMA)$_2$ was deposited on the surface of each disposable mixing well by dispensing two drops of 10% Mg(NTGGMA)$_2$/acetone into the well and evaporating the acetone solvent for one hour in air. The average amount of precipitating amine in the wells was found to be 4.0±0.21 mg. The precipitate crystallized on the base of the well and was bound to the surface.

To test adhesion of composite to dentin, two drops of PMGDM containing both camphorquinone and benzoylperoxide co-initiator were dispensed into the mixing well, stirred with a plain applicator brush, and applied to the dentin surface. Ten specimens were made and compared to the nine control specimens used in Example 7.

The average shear bond strength of the well samples was 11.22±3.60 MPa as compared to 14.21±5.37 MPa for the control mixture of solutions. There was no statistically significant difference between the two methods.

EXAMPLE 9

Combinations of Reaction Affecting Compounds

Combinations of initiators and antioxidant stabilizers can be used with this method. The speed of the polymerization reaction and delay prior to onset of polymerization, commonly called the working time, are controlled by balancing the amount of co-initiators and inhibitors within an adhesive or resin restorative material. The working time delay of polymerization onset is controlled largely by the concentration of inhibitor, such as 2,6-Di-tert-butyl-4-methylphenol (BHT). A single adhesive monomer may be used for several different substrates, e.g. enamel, dentin, metal, and porcelain, requiring customizing the working time for the different substrates and uses. Practice of this invention would provide a convenient and simple method of providing several different working times within the same system.

Methods analogous to those used for fabricating hollow fiber brushes in Examples 1 and 2 may be followed with modifications in the saturating solutions. Three different saturating solutions containing predetermined concentrations of $Mg(NTGGMA)_2$ and BHT in acetone that result in three distinctly different setting time delays may be prepared, the brush tip fibers filled and the solvent evaporated as previously described. These brush tips may then be labeled or color coded to designate the setting time resulting from their use.

The invention may be applied by mixing a single dose, two drops, of adhesive monomer containing a suitable co-initiator in a mixing well with one of the brush tips. The higher BHT containing tip is recommended for adhesive procedures to dentin where more working time is required to apply the necessary multiple coats. The mid-level BHT containing brush tip is recommended for mixing and applying the adhesive on enamel where a little working time is required, and the lowest BHT containing brush tip is recommended to mix and apply the adhesive for use on metal and ceramic surfaces where very little working time is required between mixing and polymerization.

EXAMPLE 10

Sealants

The invention may also be employed to initiate dental resins used as pit and fissure sealants. Chemically cured sealants are usually comprised of two liquid resin components that are mixed immediately before applying. One of the components contains a polymer resin (BIS-GMA) with a free radical initiator, such as benzoyl peroxide, and the other component contains a similar resin with an amine co-initiator. The resin mixture is quickly painted into the anatomical pits and fissures of previously acid-etched tooth enamel. The dispensing, mixing and application of this mixture must occur very rapidly to prevent contamination of the etched enamel with water or saliva prior to resin being applied. The present invention provides a rapid and simple manner of adding the necessary initiators and applying the resin mixture.

The brush tip may be impregnated in a manner similar to that described in Example 2. A specific quantity of amine initiator, such as dimethylparatoluidine (DMPT), may be deposited into the lumen of a hollow fiber brush tip. The quantity deposited is controlled by the concentration of acetone-amine solution used to fill the lumen. This quantity is determined to provide adequate working time and cure for a dose increment (two drops) of the sealant resin. The sealant resin may be a mixture of BIS-GMA and benzoyl peroxide, along with antioxidant stabilizers such as BHT. These same methods could be used to impregnate a sponge applicator for the sealant resin.

The invention may be used by dispensing two drops of the sealant resin into a mixing well and stirring rapidly with the impregnated sponge or brush. The sponge or brush may then be used to paint the sealant onto the previously etched surface of the tooth enamel. Once the area of interest is coated, the sponge or brush is disposed of. This procedure saves the time necessary to dispense two separate solutions prior to mixing and applying. The invention also provides savings in packaging costs and improves the asepsis of the operating environment by eliminating the second dispensing vessel.

EXAMPLE 11

Method of Determining Initiator Concentration

The amounts of initiators, co-initiators and stabilizers used in dental adhesive and resin-based materials are determined on a weight percentage of the neat resin basis. A typical example of an adhesive formulation would be the use of PMGDM adhesive resin which is a 20% solution of PMGDM in acetone. Included as initiators are 0.2%, by weight of PMGDM, camphorquinone (CQ) light initiator, 2.0%, by weight of PMGDM, benzoyl peroxide (BP) as a chemical initiator, and 0.5%, by weight of PMGDM, 2,6-Di-tert-butyl-4-methylphenol (BHT) as a stabilizer. A typical single dose of this combination would be two drops weighing approximately 0.045 grams. The corresponding dose weights of each of the contained initiators would then be calculated by:

(CQ)=0.045×0.20×0.002=0.000018 gram or 0.018 mg.

(BP)=0.045×0.20×0.02=0.00018 gram or 0.18 mg.

(BHT)=0.045×0.20×0.005=0.000045 gram or 0.045 mg.

A corresponding amine co-initiator is added to this mixture in the form of a 5% magnesium salt of NTG-GMA in acetone. In a liquid form, this is added by mixing equal volumes of the PMGDM mixture with the $Mg(NTGGMA)_2$/acetone mixture. The resulting weight of amine from two drops of this solution could then be calculated as:

$(Mg(NTGGMA)_2$=0.045×0.05=0.00225 gram or 2.25 mg.

These calculations, therefore, determine the weights of each of the initiators, co-initiators, and stabilizers that could be incorporated into the technique described by the invention. An example would be the loading of the disposable brush tips described in Examples 1, 2, and 3 with the $Mg(NTGGMA)_2$. The brush tip contains 2.25 mg of the precipitated amine salt to activate the drops of the previously described PMGDM solution. This is accomplished by dipping the brush in a 20% solution of $Mg(NTGGMA)_2$ in acetone and absorbing 11.25 mg of the solution. Once the acetone has evaporated the resulting deposited amine on the brush tip would be:

$(Mg(NTGGMA)_2 = 11.25 \times 0.20 = 2.25$ mg. This brush can then be used with a two drop dose the PMGDM solution.

EXAMPLE 12

Absorptive sponges were prepared with two different concentrations of $Mg(NTGGMA)_2$ amine in acetone. Fourteen sponges were saturated and evaporated with 8.2% $Mg(NTGGMA)_2$ in acetone and ten sponges were saturated and evaporated with 10% (NTG-GMA) in acetone. The samples with 8.2% solution resulted in 2.36±0.44 mg of deposited amine and the 10% solution resulted in 2.73±0.32 mg of deposited amine. Demonstrably, the final amount of precipitated material can be carefully controlled using the initial saturating solution concentration.

It should be understood that the foregoing disclosure emphasizes certain specific embodiments of the invention and that all modifications or alternatives equivalent thereto are within the spirit or scope of the invention as set forth in the appended claims.

What is claimed is:

1. A device for controllably affecting the desired chemical setting reaction of a chemically initiated liquid dental adhesive, resin or restorative material, said device comprising an instrument or mixing container that has a reaction affecting compound capable of affecting said desired setting reaction deposited and affixed into or onto the surface thereof, the reaction affecting compound being present in a predetermined amount sufficient to accomplish the intended reaction effect for a single application aliquot of adhesive, resin or restorative material, whereby when the instrument or container with the deposited reaction affecting material is put in contact with the adhesive, resin or restorative material the desired setting reaction takes place.

2. The device of claim 1 wherein the dental adhesive, resin or restorative material is a polymerizable monomer the polymerization of which is free-radical initiated.

3. The device of claim 1 wherein the reaction affecting compound is selected from the group consisting of a catalyst, a stabilizer, an antioxidant and an initiator.

4. The device of claim 3 wherein two or more different types of reaction affecting compounds are deposited into or onto a surface of the instrument or container.

5. The device of claim 1 wherein the instrument or mixing container is selected from the group consisting of a bristle brush, sponge, absorptive pledget, or mixing well.

6. The device of claim 1 wherein the liquid dental adhesive, resin or restorative material is a dentin bonding material; the reaction affecting compound is selected from the group consisting of N-phenylglycine, N-tolyglycine glycidylmethacrylate, N-phenylglycine glycidylmethacrylate, and the monosodium and divalent salts thereof; and the instrument is a hollow lumen brush.

7. A kit for performing dental restorative procedures comprising:

a) A chemically initiated liquid dental adhesive, resin or restorative material; and b) An instrument or mixing container with a reaction affecting compound deposited and affixed into or onto the surface thereof, said reaction affecting compound being present in a predetermined amount sufficient to accomplish an intended chemical setting reaction effect for a single dispensed aliquot of adhesive, resin or restorative material, whereby when the instrument or container with the deposited reaction affecting material is put in contact with the adhesive, resin or restorative material the desired setting reaction takes place.

8. The kit of claim 7 wherein the dental adhesive, resin or restorative material is a polymerizable monomer the polymerization of which is free-radical initiated.

9. The kit of claim 7 wherein the reaction affecting compound is selected from the group consisting of a catalyst, a stabilizer, an antioxidant and an initiator.

10. The kit of claim 9 wherein two or more different types of reaction affecting compounds are deposited into or onto a surface of the instrument or container.

11. The kit of claim 7 wherein the instrument or mixing container is selected from the group consisting of a bristle brush, sponge, absorptive pledget, or mixing well.

12. The kit of claim 7 wherein the liquid dental adhesive, resin or restorative material is a dentin bonding material; the reaction affecting compound is selected from the group consisting of N-phenylglycine, N-tolylglycine glycidylmethacrylate, N-phenylglycine glycidylmethacrylate, and the monosodium and divalent salts thereof; and the instrument is a hollow lumen brush.

* * * * *